US008636668B2

(12) United States Patent
Kawano et al.

(10) Patent No.: US 8,636,668 B2
(45) Date of Patent: *Jan. 28, 2014

(54) MEASURING APPARATUS (75) Inventors: Katsunori Kawano, Kanagawa (JP); Yoshio Nishihara, Kanagawa (JP); Yasuaki Kuwata, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 1054 days.

This patent is subject to a terminal disclaimer.

(21) Appl. No.: 12/428,569

(22) Filed: Apr. 23, 2009

(65) Prior Publication Data

US 2010/0069766 A1  Mar. 18, 2010

(30) Foreign Application Priority Data

Sep. 18, 2008  (JP) .................. 2008-239445

(51) Int. Cl.
*A61B 5/02* (2006.01)
*G01P 3/36* (2006.01)

(52) U.S. Cl.
USPC ......................... 600/504; 356/28.5

(58) Field of Classification Search
USPC .................. 600/504; 356/27–28.5
See application file for complete search history.

(56) References Cited

U.S. PATENT DOCUMENTS

| 6,323,943 B1 * | 11/2001 | Maruyama et al. ........... 356/28.5 |
| 6,707,027 B2 * | 3/2004 | Liess et al. .................... 250/221 |
| 2002/0104957 A1 * | 8/2002 | Liess et al. .................... 250/221 |
| 2007/0058157 A1 * | 3/2007 | Deines ........................... 356/28 |
| 2008/0234590 A1 * | 9/2008 | Akkermans et al. .......... 600/504 |
| 2008/0304042 A1 * | 12/2008 | Ueno ............................. 356/4.1 |
| 2009/0279070 A1 * | 11/2009 | Ueno ............................. 356/28.5 |

FOREIGN PATENT DOCUMENTS

| JP | 01-233371 | 9/1989 |
| JP | 10-009943 | 1/1998 |

OTHER PUBLICATIONS de Mul et al., "Self-mixing laser-Doppler velocimetry of liquid flow and blood perfusion in tissue" 1992. Applied Optics. vol. 31, No. 27, pp. 5844-5851.*
Koelink et al., "Laser Dopller velocimeter based on the self-mixing effect in a fiber-coupled semiconductor laser: theory" 1992. Applied Optics. vol. 31, No. 18, pp. 3401-3408.*
Gagnon and Rivest, "Laser Range Imaging Using the Self-Mixing Effect in a Laser Diode" 1999. IEEE Transactions on Instrumentation and Measurement, vol. 48, No. 3. pp. 693-699.*

(Continued)

*Primary Examiner* — Navin Natnithithadha
*Assistant Examiner* — Eric Messersmith
(74) *Attorney, Agent, or Firm* — Fildes & Outland, P.C.

(57) ABSTRACT

Provided is a measuring apparatus that includes: a semiconductor laser device that emits a laser light beam to an object to be measured; a driving unit that provides a driving signal for modulation drive of the semiconductor laser device; a first detection unit that detects a first electrical signal that corresponds to the intensity of the laser light beam modulated due to the self-coupling effect, in a first half-cycle of the driving signal; a second detection unit that detects a second electrical signal that corresponds to the intensity of a second laser light beam modulated due to the self-coupling effect, in a second half-cycle of the driving signal being in an opposite phase of the first half-cycle; a calculation unit that calculates a difference between the first and second electrical signals; and a measuring unit that measures a change in the state of the object based on the calculated difference.

6 Claims, 5 Drawing Sheets

(56) References Cited

OTHER PUBLICATIONS

Tucker and Rakic, "Laser Range Finding Using the Self-Mixing Effect in a Vertical-Cavity Surface-Emitting Laser" 2002. 2002 Conference on Optoelectronic and Microelectronic Materials and Devices, pp. 583-586.*

Gui et al., "New Laser Doppler Velocimetry with Wide Dynamic Range and Clear Directional Discrimination," 2005, Chin. Phys. Lett. vol. 22, No. 6, 1344-1346.*

\* cited by examiner

Cross sectional view taken along line A-A

Observed waveform

US 8,636,668 B2

MEASURING APPARATUS

CROSS-REFERENCE TO RELATED APPLICATION

This application is based on and claims priority under 35 USC 119 from Japanese Patent Application No. 2008-239445 filed Sep. 18, 2008.

BACKGROUND

1. Technical Field

The present invention relates to a measuring apparatus.

2. Related Art

Various types of measurement that use a semiconductor laser for measuring oscillation, distance, velocity or the like of an object to be measured are known.

Such measurements use the self-coupling effect of the laser. The self-coupling effect of the laser is an effect where returned light or reflected light of a laser beam is amplified in a laser medium, and as a result, the laser oscillation state is modulated. For a semiconductor laser with high gain, even if the returned light has an intensity of less than one hundredths that of an emitted laser light beam, the state of the returned light may be observed at a high signal to noise ratio (SNR).

When the returned light is subjected to frequency shifts due to the Doppler effect, or the position of reflection from the object to be measured is varied and is subjected to phase modulation, the oscillation state of the laser due to the self-coupling effect may vary in accordance with the changes. By analyzing the variations, the velocity or displacement of the object may be measured.

SUMMARY

An aspect of the present invention provides a measuring apparatus that includes: a semiconductor laser device that emits a laser light beam to an object to be measured; a driving unit that provides a driving signal for modulation drive of the semiconductor laser device; a first detection unit that detects a first electrical signal that corresponds to the intensity of the laser light beam modulated due to the self-coupling effect, in a first half-cycle of the driving signal; a second detection unit that detects a second electrical signal that corresponds to the intensity of a second laser light beam modulated due to the self-coupling effect, in a second half-cycle of the driving signal being in a phase opposite to that of the first half-cycle; a calculation unit that calculates a difference between the first and second electrical signals; and a measuring unit that measures a change in the state of the object based on the calculated difference.

BRIEF DESCRIPTION OF THE DRAWINGS

Exemplary embodiments of the present invention will be described in detail based on the following figures, wherein.

DETAILED DESCRIPTION

Figure 9:
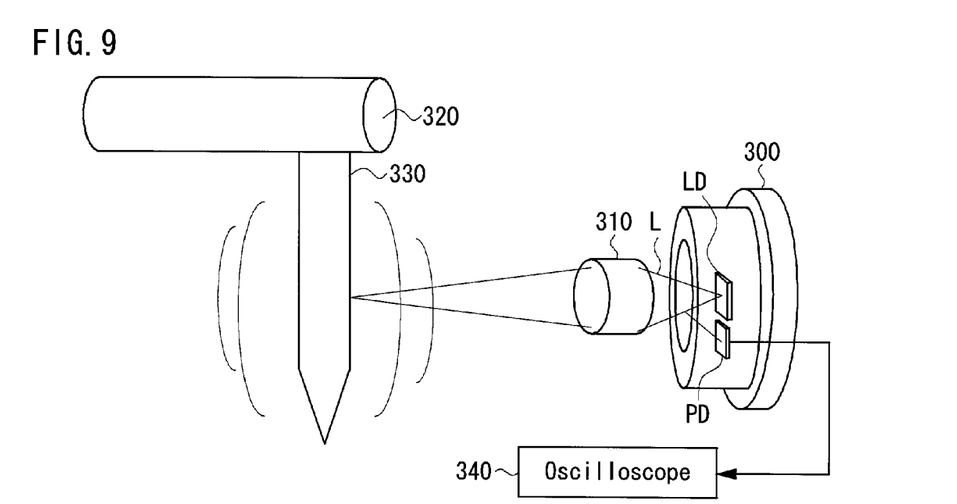
FIG. 9 illustrates an example of a configuration of a vibration measuring apparatus of a related art.

FIG. 9 illustrates an example of a general vibration measuring apparatus of a related art. As shown in FIG. 9, a laser apparatus 300 may include a laser device LD and a light receiving device (photo detector: PD.) The laser light beam L from the laser device LD through a lens 310 may irradiate a capillary 330 oscillated by an ultrasonic horn 320. The oscillation state of the laser device LD may be modulated by the self-coupling effect due to returned light reflected or scattered by the capillary 330. The modulated oscillation state of the laser device LD may be monitored by the light receiving device PD.

Figure 10:
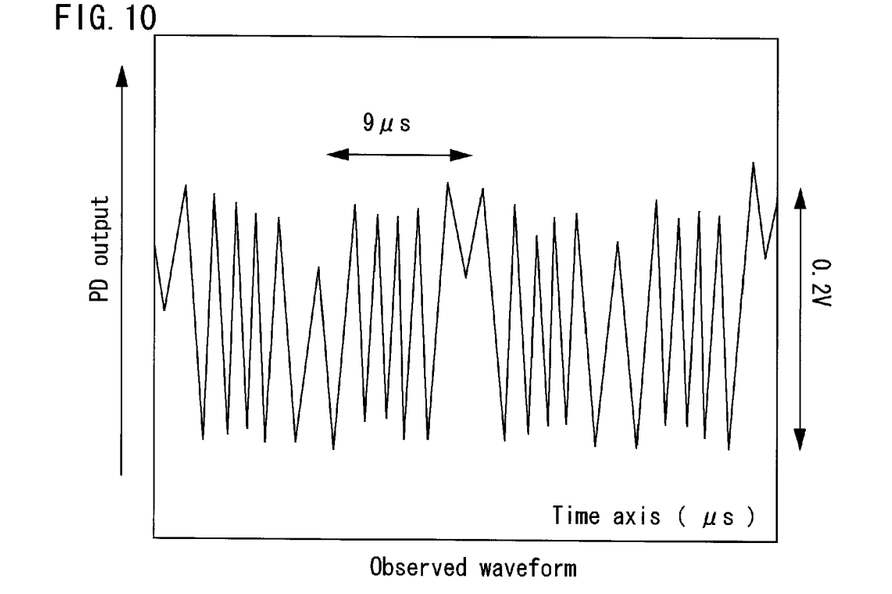
FIG. 10 illustrates an observed waveform of a vibration measuring apparatus of a related art.

FIG. 10 illustrates an observed waveform when the output signal of the light receiving device PD is coupled to an oscilloscope 340. The vertical axis shows output voltage (V) of the light receiving device, and the horizontal axis shows time (μs). As obvious from FIG. 10, in the output signal of the light receiving device PD, plural peaks having a short period are appeared in a range of about 0.2 V. These peaks mean that the laser oscillation state is modulated due to the returned light from the capillary 330, and beat signals are generated in the light intensity of the laser light beam.

If the intensity of a laser beam emitted to an object to be measured is $I_{in}$, the reflectivity of the object to be measured is r, and the self-coupling efficiency of the laser is α, then the intensity modulated due to the self-coupling effect becomes $I_{out}$ as expressed in Equation (4). Where Δω is the difference between the oscillation frequency when the laser light frequency is modulated during the measurement and the frequency of the returned light, Ω is the amount of phase-shift due to the Doppler effect upon the reflection from the object, Δd is the amount of displacement of the object to be measured, and k is the wave number vector of incident light.

$$I_{out}(t)=I_{in}+\Delta I(t)+r\alpha I_{in} \cos [(\Delta w+\Omega)t-k\Delta d] \quad (4)$$

As in Equation (4), when the object to be measured is subjected to the Doppler effect or displaced, the light intensity is oscillated as a function of cos.

Measuring apparatuses of related arts may measure changes in the state of an object to be measured, such as velocity or oscillation, by using Equation (4). However, if the reflectivity r of the object to be measured varies, the detected light intensity $I_{out}$ is modulated due to the self-coupling effect, resulting that the measurement may provide an inaccurate result that includes noises.

In an exemplary embodiment of the present invention, modulations of laser due to the self-coupling effect at different time are detected. During the process, frequency modulation of the laser light beam is performed, and modulation signals in opposite phase over time may be detected. By obtaining a difference between two signals at opposite phases, noise components due to variations in the reflectivity of the object to be measured is removed, and velocity, variations or the like may be accurately measured. In a configuration of the present invention, if the SNR of the signals due to the self-coupling effect is insufficient, it is preferable to use a lens such that the laser light beam is imaged onto the object to be measured. In contrast, in a case where a sufficient SNR is obtained, the lens is not necessary.

Examples described hereafter use a blood flow sensor that measures the velocity of hemoglobin in the blood as an example, and the velocity of an object to be measured such as hemoglobin, whose reflectivity of the surface to be irradiated readily varies, may be accurately measured.

Figure 1:
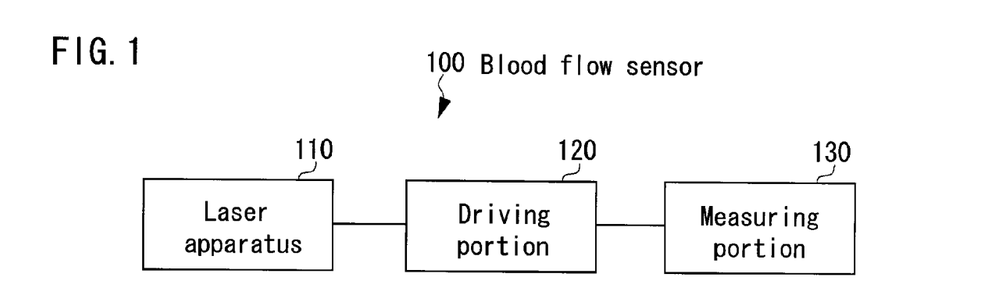
FIG. 1 is a block diagram illustrating a configuration of a blood flow sensor according to an aspect of the present invention.

FIG. 1 is a block diagram illustrating a configuration of a blood flow sensor according to an aspect of the present invention. A blood flow sensor 100 of the example may include a laser apparatus 110 having a semiconductor laser device that emits coherent laser light, a driving portion 120 that drives the semiconductor laser device, and a measuring portion 130 that measures changes in the state of an object to be measured from a signal obtained by use of the self-coupling effect.

Figure 2:
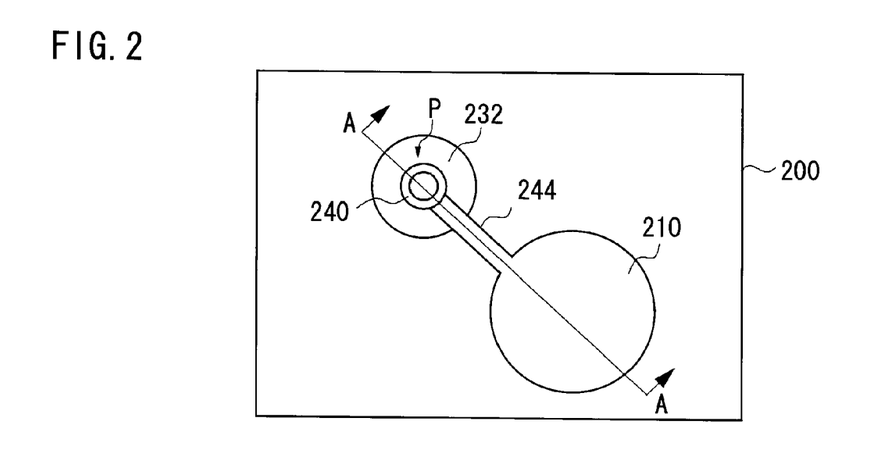
FIG. 2 is a plan view of a VCSEL device preferably used for a blood flow sensor of an example.
Figure 3:
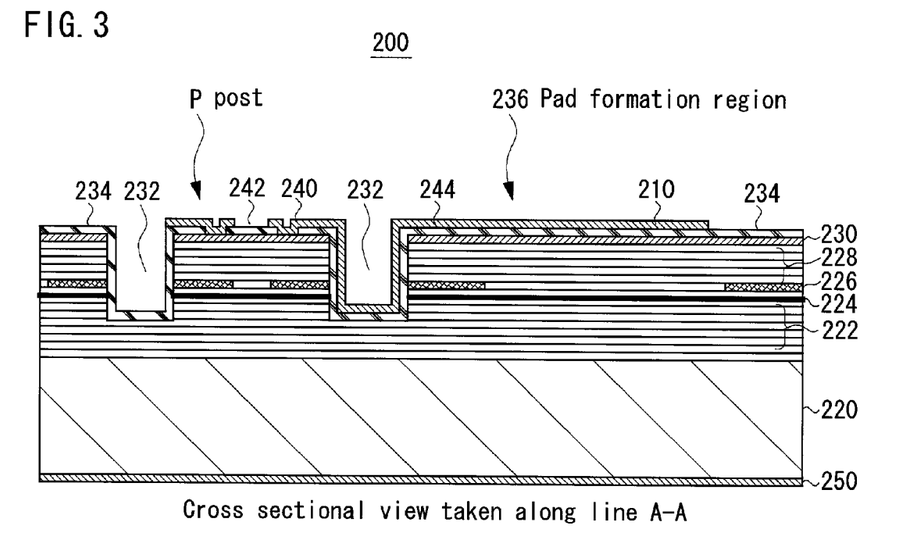
FIG. 3 is a cross sectional view taken along line A-A of FIG. 2.

The laser apparatus 110 of this example may preferably use a VCSEL as a semiconductor laser device. FIG. 2 is a plan view of a semiconductor chip on which a VCSEL is formed. FIG. 3 is a cross sectional view taken along line A-A of FIG. 2. As shown in FIG. 2, on a surface of a semiconductor chip 200, a cylindrical post (or mesa) P that becomes a light emitting portion of laser light may be formed, and an annular p-side electrode 240 may be formed at a top portion of the post P. The p-side electrode 240 may be coupled to a round electrode pad 210 by a wiring 244. The electrode pad 210 may be electrically coupled to the driving portion 120 by a coupling medium (not shown) such as a bonding wire.

As shown in FIG. 3, the semiconductor chip 200 may be formed on an n-type GaAs semiconductor substrate 220 by stacking semiconductor layers as follows: an n-type lower DBR 222 made by stacking plural AlGaAs layers each having a different Al-composition, an active region 224, a current confining layer 226 made of p-type AlAs and surrounded by an oxidized region, a p-type upper DBR 228 made by stacking plural AlGaAs layers each having a different Al-composition, and a p-type GaAs contact layer 230. Semiconductor layers over the substrate 220 may be etched to form an annular groove 232, and the cylindrical post P. An interlayer insulating film 234 may be formed to cover a bottom portion, a side portion, and a portion of the top portion of the post P. At a top portion of the post P, the p-side electrode 240 may be formed, which is electrically coupled to the contact layer 230 through a contact hole in the interlayer insulating film 234. At a center portion of the p-side electrode 240, an emission window 242 for emitting laser light may be formed. The wiring 244 may extend from the p-side electrode 240 through the groove 232 to a pad formation region 236 and may be coupled to an electrode pad therein. On the back surface of the substrate 220, an n-side electrode 250 may be formed. In the post P, the lower DBR 222 and the upper DBR 228 may form a vertical resonator. When a forward driving current is applied to the p-side electrode 240 and the n-side electrode 250, a laser light beam having a wavelength of about 850 nm is emitted from the emission window 242 of the post P vertically with respect to the substrate.

Figure 4:
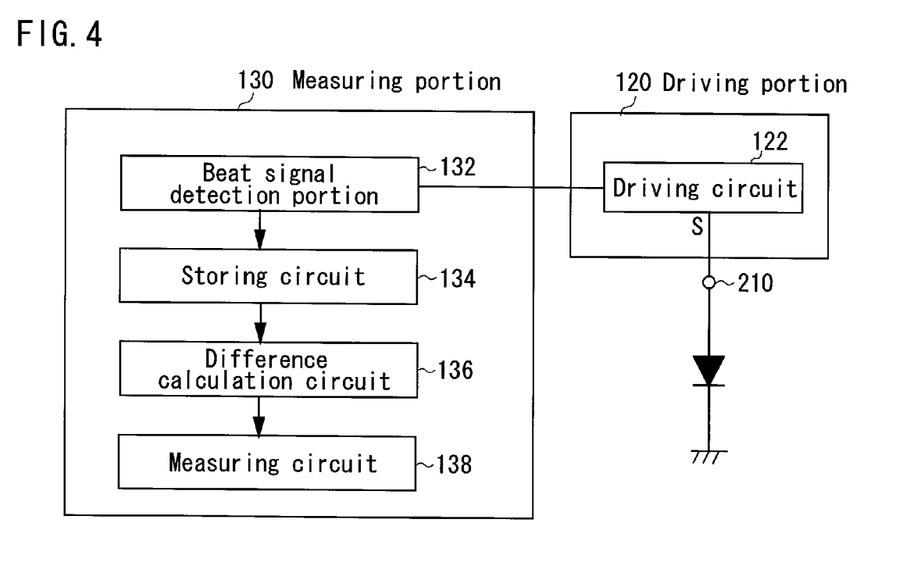
FIG. 4 illustrates an internal configuration of a driving portion and a measuring portion.

FIG. 4 is a block diagram illustrating an internal configuration of a driving portion and a measuring portion. The driving portion 120 may provide a driving signal S for driving the VCSEL to the electrode pad 210.

Figure 5:
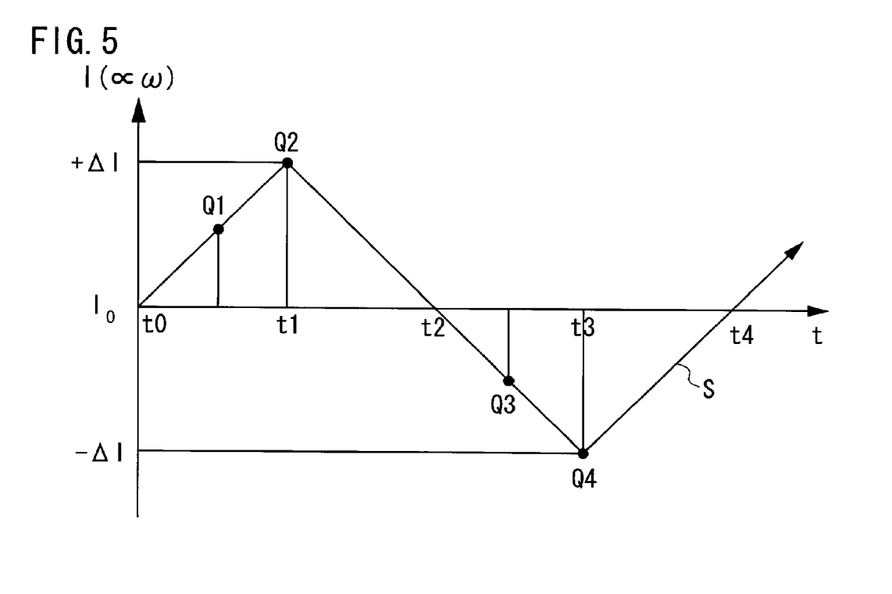
FIG. 5 illustrates a waveform of a driving signal.

FIG. 5 is a diagram illustrating a current waveform of the driving signal S. The vertical axis shows the intensity of the laser light beam, and the horizontal axis shows time. If the reference oscillation intensity of the laser beam is $I_0$, the driving signal S is a driving current of a triangular wave having a driving frequency such that the intensity changes between $+\Delta I$ and $-\Delta I$ are repeated, centering the reference oscillation intensity. In the example of FIG. 5, time t1 to t4 are one cycle, and the driving signal S is drive modulated such that the driving signal S has the reference oscillation intensity $I_0$ at time t0; an intensity of $+\Delta I$ at time t1; the reference oscillation intensity $I_0$ at time t2; and an intensity of $-\Delta I$ at time t3. For VCSELs, the driving current and the oscillation wavelength are in an approximately linear relation, and the larger the driving current becomes, the larger the oscillation wavelength becomes accordingly. Therefore, from the post P, a laser light beam having time-wise wavelength changes is emitted. The current waveform of the driving signal S is not limited to the shape as shown in FIG. 5, and may be a sawtooth shape having a waveform different from this example.

As shown in FIG. 4, the measuring portion 130 may include a beat signal detection portion 132 that detects a beat signal whose light intensity is modulated due to the laser light emitted from the post P and returned light from the object to be measured, a storing circuit 134 that stores a value detected by the beat signal detection portion 132, a difference calculation circuit 136 that calculates a difference between the beat signals having opposite phases over time, and a measuring circuit 138 that measures the state of the object to be measured based on the calculation result of the difference calculation circuit 136.

By modulating the light intensity of the semiconductor laser, the oscillation frequency can be varied. This modulation makes the oscillation frequency differ from the frequency of the returned light, and therefore modulation occurs in the laser medium, and a beat signal occurs in the light intensity. Larger the difference between the frequency of the returned light and the oscillation frequency means that the distance to the object to be measured is farther. Therefore, by analyzing the frequency of the beat signal, the distance between the laser and the object to be measured can be measured.

The beat signal detection portion 132 shown in FIG. 4 may detect a beat signal based on impedance changes in the driving signal S of a driving circuit 122. Specifically, when the laser light from the post P is emitted to an object to be measured, the returned light reflected or scattered from the object to be measured returns into the laser medium of the post P, and the laser oscillation state thereof is modulated, and a beat signal is generated in the light intensity due to the difference between the frequencies of the laser light and the returned light, and the beat signal appears as an impedance change in the driving signal.

When the modulation frequency of the driving signal S is one cycle from time t0 to t4 as shown in FIG. 4, the beat signal detection portion 132 detects a first amount of variation of the beat signal during a first half-cycle from time t0 to t2, and detects a second amount of variation of the beat signal during a second half-cycle from time t2 to t4 being in a phase opposite to that of the first half-cycle.

In the example of FIG. 4, the beat signal detection portion 132 detects beat signals each at time Q1 and time Q2, and stores detected values of the beat signals in the storing circuit 134. The beat signal detection portion 132 also detects a beat signal at time Q3 that is shifted by a half phase from time Q1, detects a beat signal at time Q4 that is shifted by a half phase from time Q2, and stores the values of the beat signals to the storing circuit 134. The difference calculation circuit 136 calculates the first amount of variation from the values of the beat signals at time Q1 and Q2 stored in the storing circuit 134, and calculates the second amount of variation from the beat signals at time Q3 and Q4.

The first and second amount of variation detected by the beat signal detection portion 132 is expressed in Equations (1) and (2).

$$I_1(Q2-Q1) = I_0 + \Delta I(Q2-Q1) + r\alpha I_0 \cos[(\Delta w + \Omega)t - k\Delta d] \quad (1)$$

$$I_2(Q4-Q3) = I_0 - \Delta I(Q4-Q3) + r\alpha I_0 \cos[(-\Delta w + \Omega)t - k\Delta d] \quad (2)$$

Where, if the intensity of the laser light emitted to the object to be measured is $I(=I_0+\Delta I)$, then $I_0$ is the reference oscillation intensity of the laser light, $\Delta I$ is the amount of modulation from the reference oscillation intensity $I_0$, r is the reflectivity of the object to be measured, $\alpha$ is the self-coupling efficiency of the laser light, $\Delta\omega$ is the difference between the oscillation frequency of the laser light emitted from the semiconductor laser device and the frequency of the reflected light, $\Omega$ is the amount of phase-shift due to the Doppler effect upon the reflection from the object to be measured, $\Delta d$ is the amount of displacement of the object to be measured, and k is the wave number vector of the reflected light.

The difference calculation circuit 136 may calculate a difference $|I_1-I_2|$ between the first and second amount of variation detected as described above. The calculated difference is expressed by Equation (3). Where the reference oscillation intensity $I_0 \gg$ the amount of modulation $\Delta I$, $Q2-Q1 \approx Q4-Q3 \ll 1$ $$I_1 - I_2 = 2\Delta I + 2\alpha I_0 \sin[(\Omega t - k\Delta d)t]\sin(\Delta wt) \quad (3)$$

Figure 6:
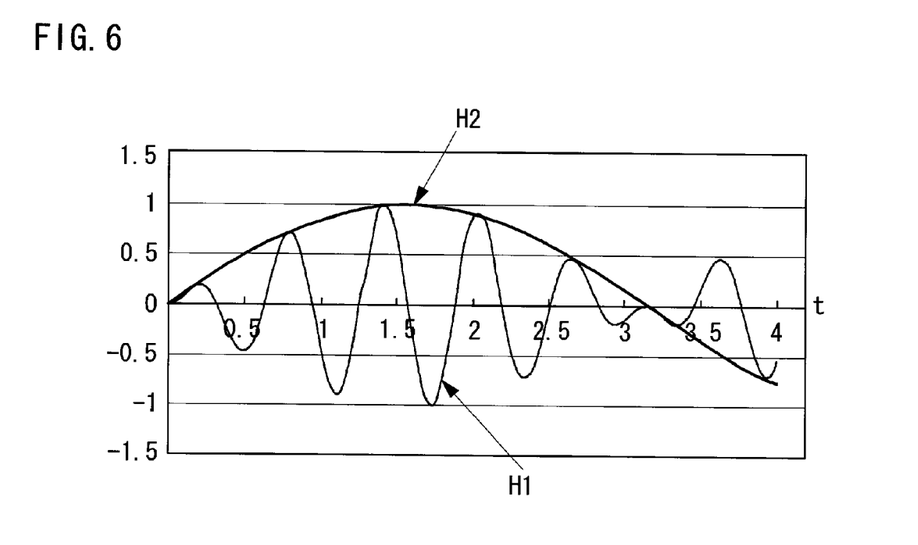
FIG. 6 illustrates a waveform of the amount of variation in a beat signal and a differential signal thereof.

FIG. 6 illustrates a waveform of the amount of variation of a beat signal and a waveform of a difference in the first and second amount of variation of the beat signal. The first and second amount of variation of the beat signal expressed by Equations (1) and (2) is a signal that beats at a short period depicted as waveform H1. The signal expressed by Equation (3), which is the difference between the first and second amount of variation, is a sinusoidal (sin) signal depicted as waveform H2.

The measuring circuit 138 is capable of measuring the velocity of hemoglobin or the blood flow amount, the object to be measured, from Equation (3) calculated by the difference calculation circuit 136. In other words, the variation of the object to be measured with respect to the oscillation at a modulation frequency $\Delta\omega$ of the laser can be detected as a beat oscillation of $\sin(\Omega t - k\Delta d)$. In addition, it should be noted that the reflectivity r of the object to be measured is removed from Equation (3). This enables that, even if the reflectivity of the object to be measured, the reflectivity of hemoglobin in this case, varies within one cycle of the driving signal S, the state of the object to be measured is measured with a high SNR without being affected by the reflectivity.

In the example described above, the amount of variation of the beat signal is detected twice during one cycle of the driving signal S. However, the invention is not limited to this example, and the amount of variation of the beat signal may be detected more times, and the difference between them can be calculated. Note that the difference should be calculated between beat signals having a relation being opposite phase one another. For example, plural measuring results may be averaged to obtain a highly accurate measuring result.

Figure 7:
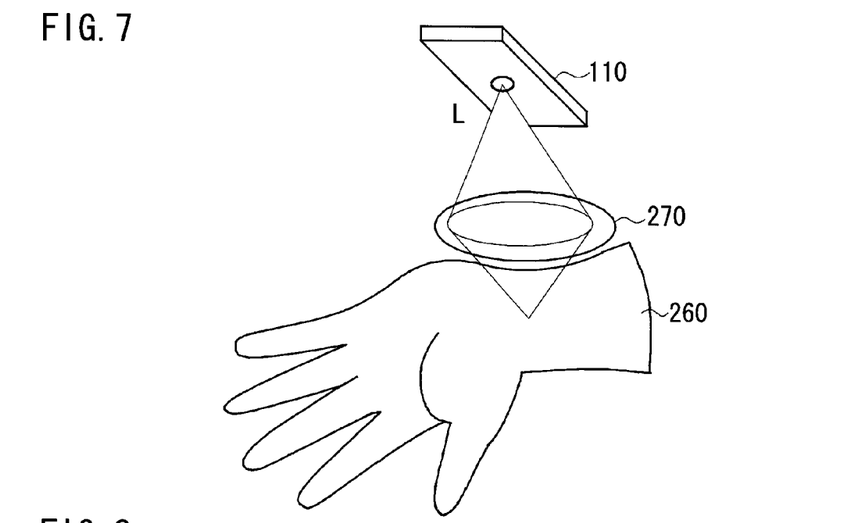
FIG. 7 illustrates an exemplary use of a blood flow sensor of an example.

FIG. 7 illustrates an exemplary use of a blood flow sensor of an example. The laser apparatus 110 of a blood flow sensor may be disposed near a human arm 260, and a laser light beam L is emitted from the light emitting portion of the laser apparatus 110 to the arm. The laser light beam having a wavelength of 850 nm may penetrate through the skin, and irradiate hemoglobin in the capillaries. A portion of reflected or scattered light from the surface of hemoglobin may contribute to the self-coupling effect as returned light, and the velocity of hemoglobin may be measured. Hemoglobin moves in the blood randomly, and the reflection surface thereof readily varies. In a measuring apparatus of a related art, variations in the reflectivity have been included as noises. However, in this example, the reflectivity r of hemoglobin in the measured Equation (3) is cancelled, and thus such noises are removed, thereby the velocity of hemoglobin, blood flow or the like can be accurately measured.

In a case where the signal of the object to be measured has an insufficient SNR, a lens 270 may be interposed between the laser apparatus 110 and the arm 260 to improve the efficiency in collecting the laser light beam L and the returned light. In addition, in the example described above, the beat signal is detected from impedance changes in the driving signal S during laser oscillation. However, other than this example, a beat signal may be detected from an output signal of a light receiving device (photo detector) that monitors the laser oscillation state of a VCSEL (see FIG. 9 and FIG. 10.) The result measured by a blood flow sensor may be outputted from a display or a speaker, for example.

Figure 8:
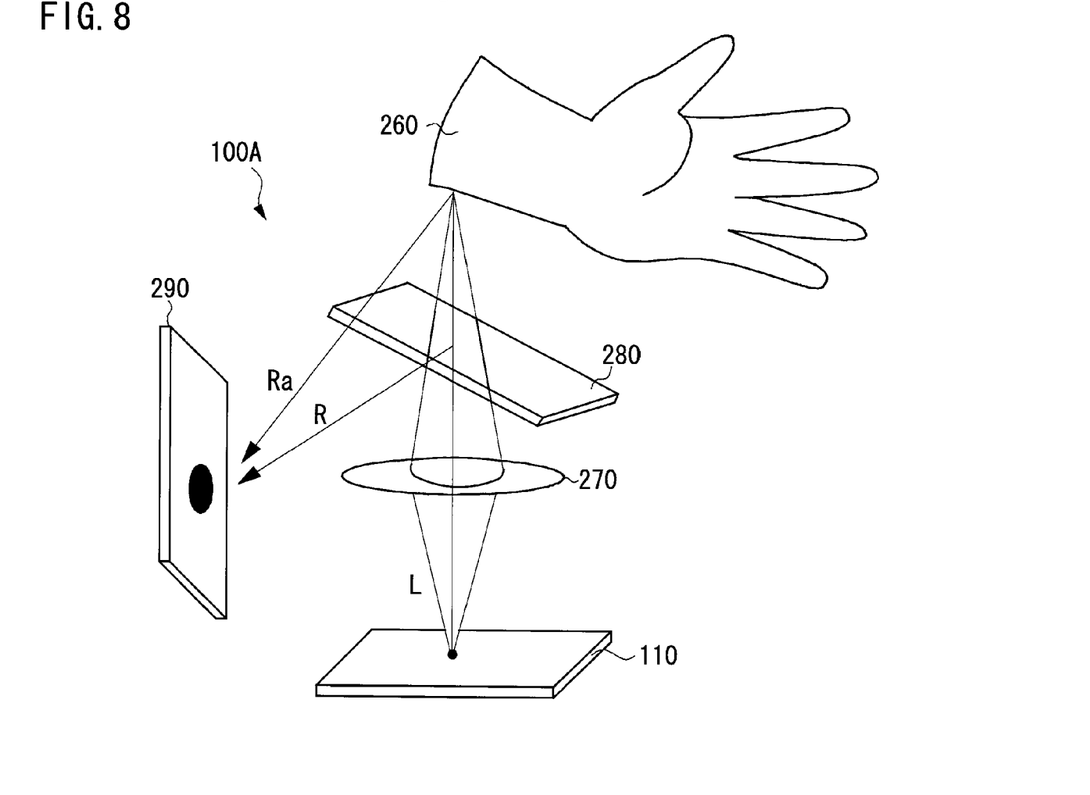
FIG. 8 illustrates a configuration of a blood flow sensor of a second example according to the present invention.

A second example of the present invention will be now described. According to the second example, as shown in FIG. 8, a blood flow sensor 100A may include a half mirror 280 and a detector 290 that detects an interference fringe. Similarly to the first example, the laser apparatus 110 may emit a drive modulated laser light beam L. The half mirror 280 may be disposed between the lens 270 and the object to be measured 260. The half mirror 280 allows a portion of the emitted laser light beam L to pass therethrough and irradiate the object to be measured 260, and allows a portion of the laser light beam L to reflect to the detector 290. With this configuration, a reflected light beam R from the half mirror 280 and a reflected light beam Ra from the object to be measured 260 may interfere with each other, and variations in the interference fringes may be detected by the detector 290. As such, a similar measurement to the measurement that uses the self-coupling effect of the first example may be done. The self-coupling effect of the first example causes interference in the laser and the interference is amplified and detected as a light intensity modulation. However, in the second example, a similar signal may be detected by an interferometer disposed out of the laser.

While exemplary embodiments of the present invention have been described in detail, the invention is not limited to these specific embodiments, and various modifications and changes can be made without departing from the inventive scope that is defined by the following claims.

In the examples described above, a single semiconductor laser device is used. However, changes in the state in a certain areas of the object to be measured may be detected by use of an array of plural semiconductor laser devices. In addition, in the examples described above, a blood flow sensor is used. However, the present invention is applicable to a non-contact measurement of oscillation, distance, displacement of an object to be measured other than blood. Moreover, in the examples described above, a VCSEL using a wavelength of 850 nm is illustrated as an example. However, a semiconductor laser device using other wavelength or having other configuration may be used.

What is claimed is:
1. A measuring apparatus comprising:
  a semiconductor laser device that emits a laser light beam to an object to be measured;
  a driving unit that provides a driving signal for modulation drive of the semiconductor laser device;
  a detection unit that detects a first electrical signal that corresponds to the intensity of the laser light beam modulated due to the self-coupling effect, in a first half-cycle of the driving signal, and that detects a second electrical signal that corresponds to the intensity of a second laser light beam emitted by the semiconductor laser device and modulated due to the self-coupling effect, in a second half-cycle of the driving signal being in a phase opposite to that of the first half-cycle;

the first electrical signal corresponding to a first amount of variation between the intensities of the laser light beam at a first time and at a second time, and the second electrical signal corresponding to a second amount of variation between the intensities of the laser light beam at a third time and at a fourth time;

a calculation unit that calculates a difference between the first electrical signal and the second electrical signal; and a measuring unit that measures a change in the state of the object to be measured based on the calculated difference;

wherein the first amount of variation and the second amount of variation is expressed in Equations (1) and (2) respectively;

$$I_1(Q2-Q1) = I_0 + \Delta I(Q2-Q1) + r\alpha I_0 \cos[(\Delta w + \Omega)t - k\Delta d] \quad (1)$$

$$I_2(Q4-Q3) = I_0 - \Delta I(Q4-Q3) + r\alpha I_0 \cos[(-\Delta w + \Omega)t - k\Delta d] \quad (2)$$

where $Q1$, $Q2$, $Q3$, and $Q4$ are the first, second, third, and fourth time, respectively, and if the intensity of the laser light beam emitted to the object to be measured is $I(=I_0+\Delta I)$, then $I_0$ is the reference oscillation intensity of the laser light beam, $\Delta I$ is the amount of modulation from the reference oscillation intensity $I_0$, r is the reflectivity of the object to be measured, $\alpha$ is the self-coupling efficiency of the laser light beam, $\Delta \omega$ is the difference between the oscillation frequency of the laser light beam emitted from the semiconductor laser device and the frequency of the reflected light, $\Omega$ is the amount of phase-shift due to the Doppler effect upon the reflection from the object to be measured, $\Delta d$ is the amount of displacement of the object to be measured, and k is the wave number vector of the reflected light; and the calculation unit is configured to calculate the difference between the first electrical signal and the second electrical signal as expressed by Equation (3);

$$I_1 - I_2 = 2\Delta I + 2\alpha I_0 \sin[(\Omega t - k\Delta d)t]\sin(\Delta wt) \quad (3)$$

where the reference oscillation intensity $I_0 \gg$ the amount of modulation $\Delta I$, and $Q2-Q1 \approx Q4-Q3 \ll 1$.

2. The measuring apparatus according to claim 1, wherein the driving signal is a driving current having a saw-tooth wave.

3. The measuring apparatus according to claim 1, wherein the detection unit detects the first and second electrical signals based on an impedance change in the driving signal.

4. The measuring apparatus according to claim 1, further comprising a light receiving device that receives a portion of the laser light beam emitted from the semiconductor laser device, wherein
the detection unit detects the first and second electrical signals based on a received signal outputted from the light receiving device.

5. The measuring apparatus according to claim 1, further comprising a lens between the semiconductor laser device and the object to be measured.

6. The measuring apparatus according to claim 1, wherein the measuring unit measuring the velocity of hemoglobin in the blood.

* * * * *